United States Patent [19]

Tachibana et al.

[11] Patent Number: 4,953,565
[45] Date of Patent: Sep. 4, 1990

[54] ENDERMIC APPLICATION KITS FOR EXTERNAL MEDICINES

[75] Inventors: Shunro Tachibana, 1-6-18, Kusagae, Chuo-ku, Fukuoka-shi, Fukuoka-ken; Uichi Shibata, Tokyo, both of Japan

[73] Assignees: Shunro Tachibana, Fukuoka; Meiji Seika Kaisha, Ltd., Tokyo, both of Japan

[21] Appl. No.: 329,913

[22] Filed: Mar. 28, 1989

Related U.S. Application Data

[63] Continuation-in-part of Ser. No. 120,555, Nov. 13, 1987, Pat. No. 4,821,740.

[30] Foreign Application Priority Data

Nov. 26, 1986 [JP] Japan ................................ 61-282703

[51] Int. Cl.$^5$ ............................................. A61N 1/00
[52] U.S. Cl. .................................. 128/798; 604/20; 604/290; 604/305
[58] Field of Search ................. 128/649, 798; 604/20, 604/22, 290, 304, 305

[56] References Cited

U.S. PATENT DOCUMENTS

| | | | |
|---|---|---|---|
| 4,309,989 | 1/1982 | Fahim | 604/290 |
| 4,557,723 | 12/1985 | Sibalis | 128/798 |
| 4,605,399 | 8/1986 | Weston et al. | 604/305 |
| 4,646,754 | 3/1987 | Seale | 128/649 |
| 4,657,543 | 4/1987 | Langer et al. | 604/290 |
| 4,702,732 | 10/1987 | Powers et al. | 128/798 |
| 4,708,716 | 11/1987 | Sibalis | 604/20 |

*Primary Examiner*—Max Hindenburg
*Attorney, Agent, or Firm*—Jordan and Hamburg

[57] ABSTRACT

An endermic application kit for external medicines comprises a container for retaining liquid containing drug, a device for supplying the liquid containing drug into the container, a drug permeable layer attached to the container to cover a bottom opening of the container, and an ultrasonic oscillator situated inside the container. When the ultrasonic oscillator and supplying device are actuated, the liquid containing drug is continuously supplied to the container, and the drug contained in the liquid is applied to a skin of a patient through the drug permeable layer by means of the ultrasonic oscillator.

4 Claims, 1 Drawing Sheet

ENDERMIC APPLICATION KITS FOR EXTERNAL MEDICINES

CROSS REFERENCE TO RELATED APPLICATION

This is a Continuation-in-Part application of Ser. No. 120,555 filed on Nov. 13, 1987, U.S. Pat. No. 4,821,740.

FIELD OF THE INVENTION

The present invention relates to endermic application kits for external medicines, with which drugs can be administered into a human body through the skin thereof with high absorption efficiency by the utilization of the function of ultrasonic oscillation.

BACKGROUND OF THE INVENTION

Means for administration of medicines to human bodies for remedy and prevention of human diseases include a method of peroral or parenteral administration by the use of an injection, a pill, a capsule, a suppository, etc. and a method of endermic administration by the use of an ointment, a drug-containing adhesive plaster, etc. Among them, the endermic administration method has almost been disregarded up to the present except the direct application of external medicines, since the endermic absorption of a drug is extremely low. (This is especially because a skin physiologically has a biological barrier function against microorganisms, chemical substances, radioactive substances, heat, etc.) Recently, however, various external medicines for endermic application are being developed through recent progress of pharmaceutical technique.

In the conventional drug-administration method by the use of peroral medicines, injections, suppositories, etc., in general, the drug concentration rapidly achieve its peak and then decreases with the lapse of time, and therefore, it is difficult to maintain a constant concentration of the drug in the blood. Even the most conventional peroral medicines have various difficult problems including the induction of gastroenteric disorders, the inactivation of the drug during the initial passage through liver after the absorption thereof from the intestine, the induction of hepatopathy, etc., and the drugs which may fully satisfy the conditions for use as a medicine are extremely limitative. In addition, the injection also has various difficult problems including the use of a needle, the induction of immunoreaction which would be caused by the direct injection of a foreign substance, etc. Furthermore, this may bring on shock or the like dangerous state, since the removal of the drug once injected into a body by injection is almost impossible.

Under the circumstances, particular attention is recently being riveted to an endermic application method, which is free from the above-mentioned defects in the case of peroral or parenteral administration methods and which can maintain the relatively constant drug concentration in blood without any dangerous immunoreaction, and an ointment or a drug-containing adhesive plaster is used for the endermic application method.

In the endermic application method by the use of such ointment, drug-containing adhesive plaster or the like, the drug is required to be transferred from the skin to the capillary bed. Since the possibility of the passage of the drug through the corneal layer or keratin layer of epidermis depends upon the various properties of the drug, including the oil-solubility, the water-solubility, the drug concentration, the pH value, the molecular weight, etc., it was difficult to maintain the sufficient drug concentration in blood by the endermic administration method. In order to solve these difficult problems, a study on the base compositions for introducing the drug into the inside of the skin by means of chemical techniques has predominantly been carried out, which resulted in success of limited base compositions for only several kinds of medicines.

SUMMARY OF THE INVENTION

The present inventors earnestly studied so as to attain the possibility of facilitating the introduction of a drug into the inside of a skin by the utilization of a physical energy in such extent that would not traumatize the skin treated, so that the drug thus introduced can pass through the corneal layer or keratin layer of epidermis with high efficiency and that the drug concentration in blood can be sufficiently maintained, and as a result, have found that the application of a drug to the surface of a skin in the presence of an ultrasonic oscillation can lead to the remarkable introduction of the drug through the skin whereby the thus-introduced drug can be absorbed into the capillary bed to cause the elevation of the drug concentration in blood. On the basis of such an unexpected discovery, the present inventors have achieved the endermic application kits for external medicines of the present invention with high endermic availability.

Drug to be applied onto the skin may be contained in a layer. However, in case a drug is included in the layer, the drug concentration in the layer decreases as the endermic application kit is operated. The present invention is to obviate this problem and to apply a drug continuously while the application kit is used.

Accordingly, in the present invention an ultrasonic oscillator is installed in a container having a drug permeable layer, wherein a drug containing liquid is continuously supplied to the container. Drug in the liquid is applied to the skin through the drug permeable layer by means of the ultrasonic oscillator. While the apparatus is operating, drug is supplied to a patient continuously at a predetermined rate.

DETAILED DESCRIPTION OF THE PREFERRED EMBODIMENTS

By selecting type of ultrasonic oscillator devices and the electric sources, various endermic application kits can be adopted with the present invention, including regular type, portable type and so on.

The ultrasonic oscillator for use in the kits of the present invention is to be electrically insulated.

Figure 1:
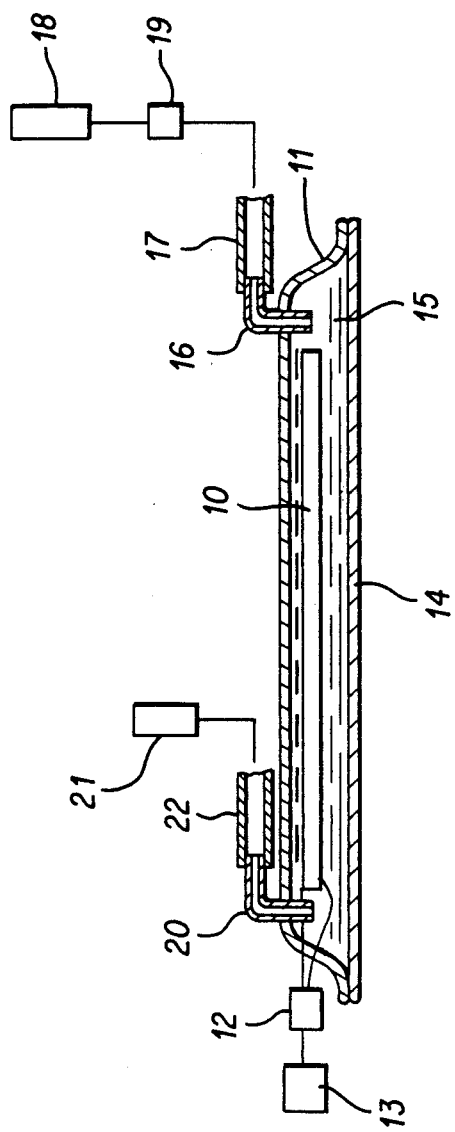
FIG. 1 shows an explanatory cross-sectional view of a portable type endermic application kit of the present invention.

On embodiment of an endermic application kit is shown in FIG. 1, wherein a disk-like ceramic ultrasonic oscillator 10 is situated in a relatively flat container 11. The oscillator 10 has a terminal 12 connected to an external oscillator device 13, which is in tern connected to a general alternating current source.

An underside of the container 11 is covered with a drug permeable layer 14, so that liquid 15 containing drug is retained inside the container 11. Unless the oscillator 10 is operated, the liquid 15 or drug does not permeate through the layer 14. The container 11 is provided with an inlet 16 connected to a tube 17, which is in turn connected to a liquid retaining section 18 through a pump 19. Further, the container 11 is provided with an outlet 20 connected to a liquid retaining section 21 through a tube 22. When the pump 19 is operated, liquid in the section 18 is transferred to the container 11 through the inlet 16, and the liquid in the container 11 is exhausted to the section 21 through the outlet 20.

In the present invention, the container 11, i.e. the drug permeable layer 14, is placed on a proper portion of a skin of a patient. Then, the pump 19 and the oscillator 10 are actuated. As a result, drug contained in the liquid is applied to the skin of the patient through the drug permeable layer 14 by means of the ultrasonic oscillator 10. Further, the liquid 15 is continuously supplied from the section 18 to the container 11 through the inlet 16, and the liquid 15 is exhausted from the container 11 to the section 21 through the outlet 20.

Namely, while the liquid 15 flows from the inlet 16 to the outlet 20, drug contained in the liquid 15 is applied to the patient through the drug permeable layer 14 by means of the ultrasonic oscillator 10. Liquid exhausted from the outlet 20, therefore, does not substantially contain drug in the liquid. In the present invention, drug can be supplied to the patient at a predetermined rate.

Also, in the present invention, it is possible to easily change concentration of the drug to be applied to the patient, or change one drug to another drug. Namely, concentration of the drug in the section 18 may be changed, or drug in the section 18 may be changed to a different drug without interruption of the operation.

Further, in the present invention, since the liquid 15 flows through the container 11, the ultrasonic oscillator 10 is always cooled. Therefore, the invention provides cooling effect relative to heat generated by oscillation of the ultrasonic oscillator 10. As a result, in the present invention, a powerful ultrasonic oscillator can be used.

Figure 2:
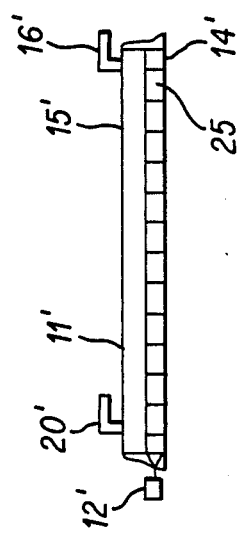
FIG. 2 shows a cross-sectional view of a different endermic application kit of the present invention.

FIG. 2 shows a different endermic application kit of the present invention, which comprises a container 11' with an inlet 16' and an outlet 20', and a drug permeable layer 14', as in the embodiment as shown in FIG. 1. However, this embodiment is provided with a flexible ultrasonic oscillator 25, such as ultrasonic oscillator film, above the drug permeable layer 14'. The oscillator 25 has a terminal 12', to be connected to an external oscillator device.

In the device as shown in FIG. 2, liquid containing drug is supplied to the container 11', continuously. Drug in the liquid is applied to the patient through the drug permeable layer 14' by means of the flexible ultrasonic oscillator 25.

In the present invention, the release rate of the drug from the kit may be controlled by decrease or increase of the output energy of the ultrasonic oscillation. Concentration of the drug in the liquid may be changed as well. The drug concentration in the blood can be freely varied.

The terminal 12, 12' can be connected to a variable oscillator device with the possibility of the free control of the drug release rate and the drug concentration in blood, and the ultrasonic oscillator device can be connected to a battery or a general electric source.

The kit being thus constituted, is suitable for application to such diseases that require an exact adjustment of the drug concentration in blood. In addition, the kit being flexible or elastic, the absorption of the drug from a fairly broad skin area is possible. A self-exciting system can also be adopted for these endermic application kits, in place of the use of the oscillator device.

Various kinds of drugs which have heretofore been used for external application, such as for ointments or drug-containing adhesive plasters, can be used in the kits of the present invention, including various slow-release drugs such as scopolamine, nitroglycerin, indomethacin, ketoprophene, calpronium chloride, etc. In addition, other drugs which were difficult to use in the form of ointments can be used in the kits of the present invention, including, for example, a high molecular insulin, various kinds of hormones, antibiotics, carcinostatics, depressors, etc. Accordingly, the continuous slow release of the drugs is possible by the use of the kits of the present invention. Moreover, the kits of the present invention can suitably be used for administration of a hypertensor to serious and emergent state patients who are difficult to ensure the blood vessel.

The administration of drugs by the use of the kits of the present invention is an endermic application by a physical technique and is therefore free from the problems in the endermic application by a chemical technique which would be limited because of the solubility and size of the molecules of the drug to be administered. Accordingly, the utility value of the kits of the present invention is extremely high.

As mentioned above, in the use of the kit of the present invention, the drug can be applied to the skin while an ultrasonice oscillation is applied thereto, and therefore, the introduction of the drug into the skin is good and the endermic administration of the drug through the skin can be carried out with extremely high efficiency. In addition, the control of the drug concentration in blood can rapidly be carried out by the control of the release rate of the drug from the kit.

While the invention has been explained with reference to the specific embodiments of the invention, the explanation is illustrative and the invention is limited only by the appended claims.

What is claimed is:

1. An endermic application kit for external medicines, comprising:
   a container for retaining liquid containing drug, said container having a bottom opening, an inlet for the liquid, and an outlet for the liquid,
   means for supplying the liquid containing drug into the container,
   a drug permeable layer attached to the container to cover the bottom opening of the container, and
   an ultrasonic oscillator situated inside the container so that when the ultrasonic oscillator and supplying means are actuated, the liquid containing drug is continuously supplied to the container and the drug contained in the liquid is applied to a skin of a patient through the drug permeable layer by means of the ultrasonic oscillator.

2. An endermic application kit according to claim 1, wherein said supplying means continuously supplies the liquid containing drug into the container through the inlet and removes the liquid in which the drug is consumed through the outlet.

3. An endermic application kit according to claim 2, further comprising an external oscillator device connected to the ultrasonic oscillator.

4. An endermic application kit according to claim 3, wherein said inlet is situated at one side of the container, and the outlet is situated at the other side away from the inlet.

* * * * *